United States Patent [19]

Hirata et al.

[11] Patent Number: 4,755,596
[45] Date of Patent: Jul. 5, 1988

[54] OPTICALLY ACTIVE CARBACEPHEMS

[75] Inventors: Tadashi Hirata, Yokohama; Yukio Hashimoto, Yamato; Takehiro Ogasa; Shigeru Kobayashi, both of Machida; Ikuo Matsukuma, Yokkaichi; Kazuo Kimura, Hofu, all of Japan

[73] Assignee: Kyowa Hakko Kogyo Co., Ltd., Tokyo, Japan

[21] Appl. No.: 921,193

[22] Filed: Oct. 21, 1986

Related U.S. Application Data

[63] Continuation of Ser. No. 789,921, Oct. 21, 1985, abandoned, which is a continuation of Ser. No. 694,903, Jan. 25, 1985, abandoned, which is a continuation of Ser. No. 574,951, Jan. 30, 1984, abandoned, which is a continuation of Ser. No. 379,342, May 18, 1982, abandoned, which is a continuation of Ser. No. 211,698, Dec. 7, 1980, abandoned, which is a continuation-in-part of Ser. No. 119,441, Feb. 7, 1980, abandoned.

[30] Foreign Application Priority Data

Feb. 10, 1979 [JP] Japan .................................. 54-14534

[51] Int. Cl.$^4$ .................. C07D 487/04; A61K 31/44
[52] U.S. Cl. .................................................... 540/205
[58] Field of Search ........................................ 540/205

[56] References Cited

U.S. PATENT DOCUMENTS 4,278,793 7/1981 Durkheimer ........................ 546/183

OTHER PUBLICATIONS

Kyowa I & II, Chem. Abs., 92, 41769a & 76269m.
Hirata I, Chem. Abs., 93, 150115a, (1980).
Hirata II, Chem. Abs., 93, 168136, 168137, (1980).
Uyeo, Chem. Pharm. Bull., 28, 1563, (1980).

Primary Examiner—Mark L. Berch
Attorney, Agent, or Firm—Fitzpatrick, Cella, Harper & Scinto

[57] ABSTRACT

Disclosed are optically active acylated cephalosporin analogs which are useful as antibacterial agents and methods for preparing such compounds.

13 Claims, No Drawings

OPTICALLY ACTIVE CARBACEPHEMS

RELATED APPLICATIONS

This application is a continuation of application Ser. No. 789,921 filed Oct. 21, 1985, now abandoned, which is a continuation of application Ser. No. 694,903 filed Jan. 25, 1985 abn which is a continuation of application Ser. No. 574,951 filed Jan. 30, 1984 now abandoned, which is a continuation of application Ser. No. 379,342 filed May 18, 1982, now abandoned, which is a continuation of application Ser. No. 211,698 filed Dec. 7, 1980, now abandoned, which is a continuation-in-part of appln. Ser. No. 119,441 filed Feb. 7, 1980, now abandoned.

BACKGROUND OF THE INVENTION

The present invention relates to optically active cephalosporin analogs and, more particularly, it pertains to optically active compounds of cephalosporin analogs represented by the general formula (I)

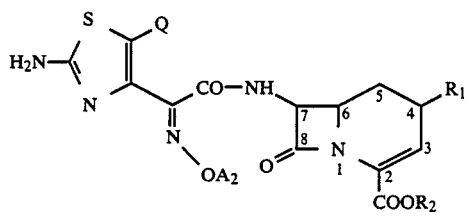

wherein $R_1$ represents a hydrogen or a lower alkyl group having 1 to 5 carbon atoms, $R_2$ represents a hydrogen or a protective group of carboxylic acid selected from straight or branched alkyl groups having 1 to 5 carbon atoms, straight or branched lower alkoxymethyl groups having 1 to 5 carbon atoms, straight or branched halogenated alkyl groups having 1 to 5 carbon atoms, lower alkylsulfonylethyl groups, arylmethyl groups having 7 to 12 carbon atoms, substituted silyl groups, substituted arylmethyl groups having 7 to 20 carbon atoms and a group represented by the formula (VI)

wherein $R_3$ is a straight or branched lower alkyl group having 1 to 6 carbon atoms, a straight or branched lower alkoxy group having 1 to 6 carbon atoms or a phenyl group and $R_4$ is a hydrogen or a straight or branched lower alkyl group having 1 to 6 carbon atoms, Q represents a hydrogen or a halo group selected from bromo, chloro, fluoro and iodo, $A_2$ represents a hydrogen, a lower alkyl group having 1 to 6 carbon atoms, a lower alkenyl group having 2 to 6 carbon atoms, a lower alkinyl group having 2 to 6 carbon atoms, a cycloalkyl group having 3 to 6 carbon atoms or an aryl group, those groups being unsubstituted or substituted with suitable substituent(s) which are selected from carboxyl group, cyano group, a halo group, carbamoyl group and a lower alkyloxycarbonyl group having 1 to 4 carbon atoms, and the hydrogens at the 6- and 7-positions have cis configuration and pharmaceutically acceptable salts thereof.

Heretofore, a carbacephem compound, which is named according to the nomenclature in J. Am. Chem. Soc. 96, 7584 (1974), wherein the sulfur atom of cephalosporin is replaced with a $CH_2$ and which has a substituted methyl group at the 3-position is described in the above reference and J. Med. Chem. 20, 551 (1977). However, no compound having especially strong antibacterial activity has been reported. In Japanese Published Unexamined Patent Application No. 9296/79 (German Offenlegungsschrift No. 2716707), a compound represented by the general formula (I) wherein $R_1$, $R_2$ and Q are a hydrogen and $A_2$ is a methyl group is mentioned but neither practical embodiment for preparing the compound nor antibacterial activity thereof is described in the reference.

The present inventors have succeeded in preparing carbacephem compounds having various substituents at the 4-, 5- or 3-position, numbering system of which is as shown in formula (I). The compounds are described in the specifications of Japanese Published Unexamined Patent Application No. 128591/79, G.O. No. 2911786, Japanese Patent Application No. 162008/78 now Japanese Published Patent Application No. 87791/80 and U.S. patent application Ser. No. 23,645 filed on Mar. 23, 1979. "G.O." refers to German Offenlegungsschrift hereinafter.

Furthermore, the present inventors have succeeded in preparing novel acylated carbacephems which are new antibiotics having strong antibacterial activities. The compounds are described in the specification of Japanese Published Unexamined Patent Application No. 128591/79, G.O. No. 2911787, U.S. patent application Ser. No. 125,861, filed Feb. 29, 1980 and Japanese Published Patent Application No. 87791/80.

Among the compounds which were provided by the present inventors and represented by the general formula (II)

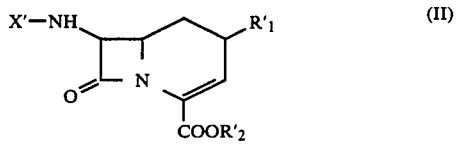

(wherein X' is a conventional acyl group employed in the chemistry of cephalosporins and penicillins, $R'_1$ represents a hydrogen atom, a lower alkyl group or a lower acyloxy group, and $R'_2$ represents a hydrogen atom or an ester-protecting group conventionally employed in the field of the chemistry of penicillins and cephalosporins, that is, an alkyl group having 1 to 5 carbon atoms such as methyl group, ethyl group, n-propyl group, isopropyl group, n-butyl group, isobutyl group, t-butyl group, etc., a halogenated alkyl group having 1 to 5 carbon atoms such as chloromethyl group, 2,2,2-trichloroethyl group, 2,2,2-trifluoroethyl group, etc., an arylmethyl group having 7 to 20 carbon atoms such as benzyl group, diphenylmethyl group, triphenylmethyl group, etc., an arylmethyl group having 7 to 20 carbon atoms and having methoxy group, nitro group, etc. on the phenyl ring, a substituted silyl group such as trimethylsilyl group or triphenylsilyl group or a group enzymatically or nonenzymatically readily eliminable in vivo, for example, a group represented by the general formula

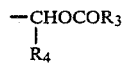

wherein $R_4$ represents a hydrogen atom or a lower alkyl group having 1 to 6 carbon atoms, $R_3$ represents a lower alkyl group having 1 to 6 carbon atoms, a lower alkoxy group having 1 to 6 carbon atoms or phenyl group, etc.), the acyl compound represented by the formula (I')

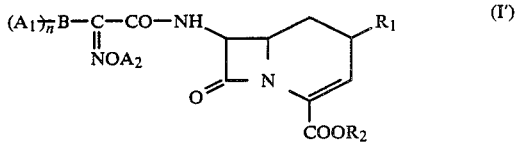

(wherein $R_1$, $R_2$ and $A_2$ have the same meanings as defined above, B represents an unsaturated six membered carbocycle which is selected from cyclohexenyl group, cyclohexadienyl group and phenyl group or a five or six membered heterocycle, $A_1$ represents substituent(s) which is selected from hydrogen atom, hydroxyl group, a lower alkoxy group having 1 to 4 carbon atoms, a halo group, nitro group, amino group, aminomethyl group, methylsulfonamide group and a lower acyloxy group having 1 to 4 carbon atoms, and n is a number of 0 to 5) which has the carbacephem ring represented by the formula (III) (shown below) are reported to have strong antimicrobial activity against Gram-positive and Gram-negative microorganisms in Japanese Patent Application Nos. 122402/78, 133071/78, 162006/78, 162007/78, published respectively as Japanese Published Unexamined Patent Applications Nos. 49375/80, 59185/80, 87789/80 and 87790/80, (German Offenlegungsschrift No. 2911787), etc. Especially the acyl compounds having the carbacephem ring represented by the general formula (I'')

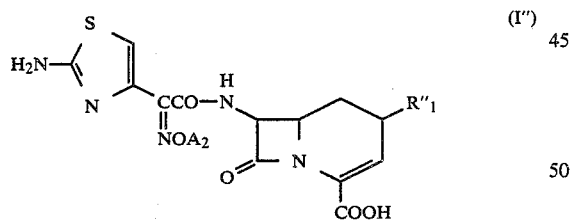

wherein $A_2$ has the same significance as defined above, $R''_1$ represents a hydrogen or a methyl group and $OA_2$ has syn configuration are reported to have strong antimicrobial activity against Gram-positive and Gram-negative microorganisms in the aforementioned patent applications. Hereinafter, compounds represented by the general formula (I), (II), (III), . . . are identified as Compound [I], Compound [II], Compound [III], . . . , respectively.

Sine cephalosporin analogs mentioned above are prepared by totally synthetic methods using optically inactive starting materials and reagents, they are optically inactive unless they have a certain optically active acyl group such as D-phenylglycyl group described in the specification of Japanese Published Patent Application No. 87789/80 and U.S. patent application Ser. No. 125,861 (German Offenlegungsschrift No. 2911787).

Accordingly, there is a demand for optically active analogs and methods for production thereof. To this end, it has now been found that certain optically active carbacephem compounds can be prepared which have unexpectedly increased biological activity.

SUMMARY OF THE INVENTION

In accordance with the present invention optically active acyl compounds represented by the above formula (I) are prepared from optically active compounds of the cephalosporin analogs represented by the general formula (III)

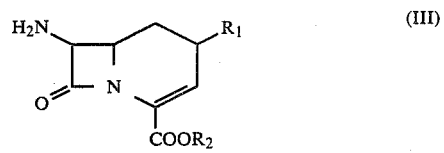

(wherein $R_1$ and $R_2$ have the same significance as defined above and hydrogens at the 6- and 7-positions have cis configuration). The compounds of the present invention have unexpectedly greater antibacterial activity, i.e. 2 to 4 times greater activity against various Gram-positive and Gram-negative microorganisms than the corresponding optically inactive dl-Compound [I].

Optically active Compound [III] and processes for preparing the same are described in commonly owned U.S. patent application Ser. No. 119,451 filed Feb. 7, 1980 of the present inventors which description is expressly incorporated herein by reference.

However, for ease of reference, suitable processes are also set forth hereinafter in Reference Examples 2 to 5.

Optically inactive dl-compounds corresponding to Compound [III] are present as a mixture of equal amounts of optical isomers (III-1) and (III-2) which are mirror images of each other (enantiomers).

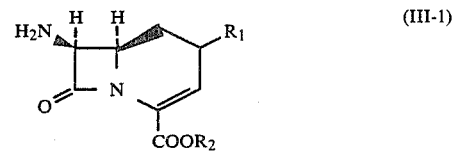

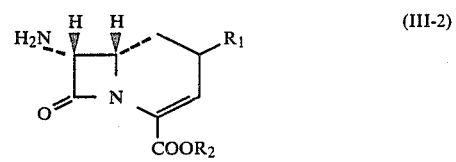

wherein $R_1$ and $R_2$ have the same significance as defined above.

The optically active compounds obtained by the processes in Reference Examples below are assumed to have the absolute structure represented by the general formula (III-1) defined above from various properties, strong antimicrobial activity of the acyl compounds compared with the corresponding optically inactive dl-compound and the relationship between the absolute structure of cephalosporins and activities thereof.

In the following description, the optically active compounds are described as having the absolute configuration of (6R, 7S), i.e. the configuration illustrated by the general formula (III-1) and in the following Examples and Reference Examples, the compounds are named according to the assumed absolute structural formula. It is needless to say that the optically active compounds are more useful as medicine and antimicrobial agents compared with optically inactive compounds and the compounds of the present invention are, therefore, useful as antibacterial agents which may be employed in manners well known in the art.

DETAILED DESCRIPTION OF THE INVENTION

The compounds of the present invention are the optically active compounds of cephalosporin analogs represented by the general formula (I)

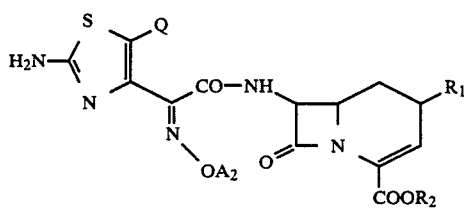

$R_1$ represents a hydrogen or a lower alkyl group having 1 to 5 carbon atoms such as methyl group, ethyl group, n-propyl group, i-propyl group, n-butyl group, i-butyl group, t-butyl group, and the like are exemplified. Particularly, among alkyl groups, methyl group is preferred. Furthermore, it is preferable that the methyl group has the same configuration as the hydrogen atoms at the 6- and 7-positions, i.e. 4α-configuration in the structural formula (III-1). However, the compounds having 4β-methyl group and the mixed compounds of 4α- and 4β-methyl compounds are valuable enough.

$R_2$ is a hydrogen atom or a protective group of carboxylic acid used in the chemistry of penicillins and cephalosporins.

Suitable $R_2$ groups are selected from:

straight or branched alkyl groups having 1 to 5 carbon atoms such as methyl group, ethyl group, n-propyl group, i-propyl group, n-butyl group, i-butyl group, t-butyl group, and the like;

straight or branched lower alkoxymethyl groups having 1 to 5 carbon atoms such as methoxymethyl group, ethoxymethyl group, and the like;

straight or branched halogenated alkyl groups having 1 to 5 carbon atoms such as chloromethyl group, 2,2,2-trichloromethyl group, 2,2,2-trifluoroethyl group, and the like;

lower alkylsulfonylethyl groups such as methylsulfonylethyl group, ethylsulfonylethyl group, and the like;

arylmethyl group having 7 to 12 carbon atoms such as benzyl group, diphenylmethyl group, trityl group, triphenylmethyl group, and the like;

substituted silyl groups such as trimethylsilyl group, triphenylsilyl group, and the like;

substituted arylmethyl groups having 7 to 20 carbon atoms wherein the substituent is methoxy group or nitro group and number of substituents on the phenyl ring is 1 to 5;

protective groups of carboxylic acid represented by the general formula (VI)

wherein $R_3$ is a straight or branched lower alkyl group having 1 to 6 carbon atoms, a straight or branched lower alkoxy group having 1 to 6 carbon atoms, or a phenyl group, and $R_4$ is a hydrogen or a straight or branched lower alkyl group having 1 to 6 carbon atoms.

Q represents a hydrogen or a halo group selected from bromo, chloro, fluoro and iodo.

$A_2$ represents a hydrogen atom, a lower alkyl group having 1 to 6 carbon atoms, a lower alkenyl group having 2 to 6 carbon atoms, a lower alkinyl group having 2 to 6 carbon atoms, a cycloalkyl group having 3 to 6 carbon atoms or an aryl group, those groups being unsubstituted or substituted with suitable substituent(s) which is selected from carboxyl group, cyano group, a halo group, carbamoyl group and a lower alkyloxycarbonyl group having 1 to 4 carbon atom.

In general, it is known that thiazolyl group represented by

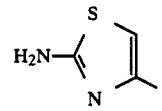

exhibits reversible interconversion with the thiazolinyl group as shown below, and both are usually regarded as identical. In the present specification, both isomers are represented by thiazolyl group. Of course, Compound [I] includes the both isomers based on the reversible interconversion.

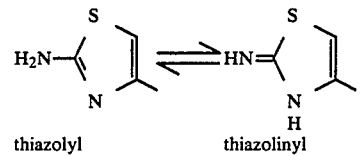

thiazolyl      thiazolinyl

As for $OA_2$, syn configuration means isomer (A) in the following representation of the stereoisomers.

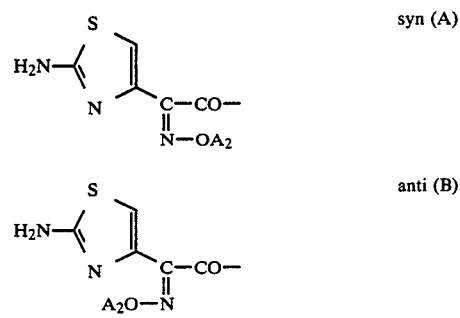

As the pharmaceutically acceptable salts of the compounds of the invention, salts of the inorganic or organic bases, for example, the alkali metal salts such as sodium salts, potassium salts, etc., alkali earth metal salts such as magnesium salts, etc., ammonium salts, trimethylamine salts, triethylamine salts, pyridine salts, procaine salts, purine salts, lysine salts, arginine salts, etc.

and salts of inorganic or organic acid, for example, hydrochloride, sulfate, carbonate, phosphate, formate, trifluoroacetate, malate, etc. are exemplified. The pharmaceutically acceptable salts are prepared by the standard methods known in the art.

The compounds of the present invention are produced by acylating an optically active compounds represented by the general formula (III-1)

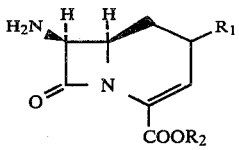

(wherein $R_1$ and $R_2$ have the same meanings as defined above) or a functionally equivalent compound with carboxylic acid represented by the general formula (VII)

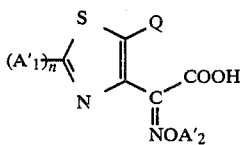

[wherein Q and n have the same significance as defined above, $A'_1$ represents a substituent which is selected from an amino group and a protected amino group, and $A'_2$ has the same significance as $A_2$ in which carboxy substituent, if any, is protected.] or with reactive derivatives of the carboxylic acid and, thereafter, optionally eliminating the protecting group in the group

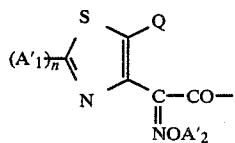

and/or $-COOR_2$ and optionally converting the acylated compounds to pharmaceutically acceptable salts.

A known acylating method is concretely described in Japanese Published Unexamined Patent Application No. 49375/80 and U.S. patent application Ser. No. 125,861 filed Feb. 29, 1980 (German Offenlegungsschrift No. 2911787).

Isolation and purification of the desired compound are carried out by conventional methods used in organic chemistry.

The invention includes within its scope pharmaceutical compositions comprising, as an active ingredient, Compound [I] or a pharmaceutically acceptable salt thereof in association with a pharmaceutical carrier or diluent. The compounds of this invention are administered by parenteral (intramuscular, intraperitoneal, intravenous or subcutaneous injection route), oral or rectal route of administration and can be formulated in dosage forms appropriate for each route of administration.

Preparations according to this invention for parenteral administration include sterile aqueous or non-aqueous solutions, suspensions and emulsions. Examples of non-aqueous solvents or vehicles are propylene glycol, polyethylene glycol, vegetable oils such as olive oil, and injectable organic esters such as ethyl oleate. Such dosage forms may also contain adjuvants such as preserving, wetting, emulsifying, and dispersing agents. They may be sterilized by filtration through a bacteria-retaining filter, by incorporating sterilizing agents into the compositions, by irradiating the compositions, or by heating the compositions. They can also be manufactured in the form of sterile solid compositions which can be dissolved in sterile water or some other sterile injectable medium immediately before use.

Compositions for oral administration may be presented in a form suitable for absorption by the gastrointestinal tract. Tablets and capsules for oral administration may be in unit dose presentation form, and may contain conventional excipients such as binding agents, for example, syrup, acacia, gelatin, sorbitol, tragacanth and polyvinylpyrrolidone; fillers, for example, lactose, sugar, maize-starch, calcium phosphate, sorbitol and glycine; lubricants, for example, magnesium stearate, talc, polyethylene glycol and silica; disintegrants, for example, potato starch and acceptable wetting agents such as sodium lauryl sulfate.

The tablets may be coated according to methods well known in the arts. Oral liquid preparations may be in the form of aqueous or oily suspension, solution, emulsion, syrup, etc. or may be presented as a dry product, for reconstitution with water or other suitable vehicle before use. The liquid preparations may contain conventional additive such as suspending agents, for example, sorbitol syrup, methyl cellulose, glucose sugar syrup, gelatin, hydroxyethylcellulose, carboxymethylcellulose and aluminum stearate gel; emulsifying agents, for example, lecithin and sorbitan monooleate; non-aqueous vehicles which may include edible oils, for example, almond oil and coconut oil, propylene glycol and ethyl alcoho; and preservatives, for example, methyl or propyl p-hydroxybenzoates and sorbic acid.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The dosage is selected depending upon the desired therapeutic effect, the route of administration, and the duration of the treatment. Generally, the present compound is administered to mammalian patients in a dose of 5 to 350 mg/kg of body weight per day to achieve an antibiotic effect.

Certain specific embodiments of the invention are illustrated by the following representative examples.

EXAMPLE 1

Preparation of (+)-cis-7-[2-(2-amino-4-thiazolyl)-2-syn-methoxyiminoacetamido]-1-azabicyclo[4,2,0]oct-2-en-8-on-2-carboxylic acid (cis refers to the stereochemistry at the 6- and 7-positions and the same shall apply hereinafter by the following steps):

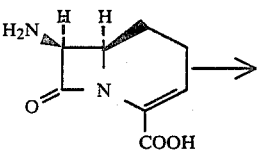

-continued

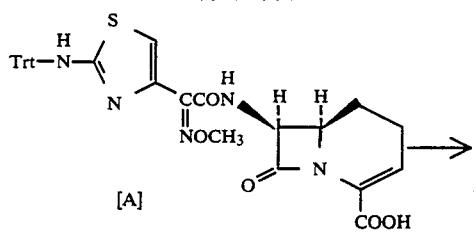
[A]

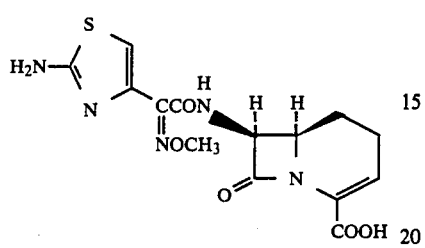

In this Example, 131.3 mg (0.30 m mole) of 2-(2-tritylamino-4-thiazolyl)-2-syn-methoxyimino acetic acid is dissolved in 1 ml of anhydrous dichloromethane and then 4.1 μl of triethylamine is added at a temperature of −20° C.

After adding 61.7 mg of phosphorus pentachloride, the mixture is stirred at a temperature of −20° C. for 30 minutes. The reaction mixture is concentrated under reduced pressure and the residue is dissolved in 1 ml of anhydrous tetrahydrofuran to obtain an acid chloride solution.

Separately, 40.2 mg (0.17 m mole) of the monohydrate of the hydrochloride of (+)-cis-7-amino-1-azabicyclo[4,2,0]oct-2-en-8-on-2-carboxylic acid obtained as in Reference Example 2 is dissolved in a mixture of 1 ml of tetrahydrofuran and 1 ml of water and 116.2 μl of triethyl amine is added thereto.

With stirring under ice cooling, the acid chloride solution prepared above is added dropwise to the solution and the mixture is allowed to react for one hour. The reaction solution is adjusted to a pH of 2.0 with 5% hydrochloric acid and extracted three times with 10 ml of ethyl acetate. The ethyl acetate layer is washed with 10 ml of saturated saline solution, dried with sodium bicarbonate, and concentrated under reduced pressure to obtain 93 mg of a crude compound [A]. The compound is dissolved in 10 ml of 50% acetic acid and the solution is stirred at a temperature of 50° C. for 30 minutes. After cooling to room temperature and removing a deposited white precipitate by filtration, the reaction solution is concentrated and the residue is dissolved in a small amount of dimethylsulfoxide. The solution is then charged on a column packed with 10 ml of HP-10 (product of Mitsubishi Kasei Kogyo Co., Ltd.). Elution is carried out with water to a mixture of water and methanol (1:2). Fractions showing an Rf value of 0.3 by silica gel thin layer chromatography [plate: Merck Art. 5719 (Product of E. Merck & Co.], solvent: butanol:acetic acid:water=4:1:1] are combined and concentrated under reduced pressure to obtain 13.5 mg (yield 22.4%) of white crystals of the desired compound having the following properties:

m.p. 172° C. (decomposition).
$[\alpha]_D^{15°}$ +32.6° (DMSO, c=0.5).
IR(KBr) $\nu_{max}^{cm-1}$: 1765, 1660, 1630, 1545.

PMR(DMSO-d$_6$)δ9.26(1H, d), 7.19(2H, s), 6.75(1H, s), 6.28(1H, t), 5.50(1H, d-d, J=8.9, 4.7), 3.83(3H, s), 2.5–1.0(4H, m).

These values coincide well with those of the corresponding dl-compound. From the strong antimicrobial activity, absolute configuration of this compound is assumed to be (6R, 7S).

EXAMPLE 2

Preparation of (−)-cis-7β-[2-(2-amino-4-thiazolyl)-2-syn-methoxyiminoacetamido]-4α-methyl-1-azabicyclo[4,2,0]oct-2-en-8-on-2-carboxylic acid.

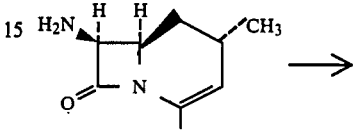

[B]
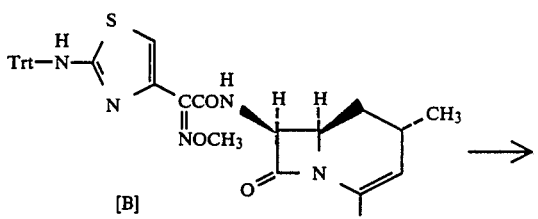

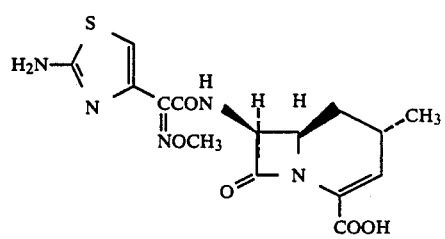

In this Example, 76 mg (0.17 m mole) of 2-(2-tritylamino-4-thiazolyl)-2-syn-methoxyimino acetic acid is dissolved in 1.52 ml of anhydrous dichloromethane and 17.3 mg (0.17 m mole) of triethylamine is added thereto at a temperature of −15° C. After adding 35.7 mg (0.17 m mole) of phosphorus pentachloride, the mixture is stirred at a temperature of −15° C. for 30 minutes. The reaction mixture is concentrated under reduced pressure and the residue is dissolved in 2 ml of anhydrous tetrahydrofuran to obtain an acid chloride solution.

Separately, 28 mg (0.10 m mole) of the dihydrate of the potassium salt of (−)-cis-7β-amino-4α-methyl-1-azabicyclo[4,2,0]oct-2-en-8-on-2-carboxylic acid obtained as in Reference Example 4 is suspended in a mixture of 1.5 ml of tetrahydrofuran and water (1:1) and 36.3 mg (0.36 m mole) of triethylamine is added thereto to make a homogenous solution. With stirring under ice cooling, the acid chloride solution is added dropwise to the solution and the mixture is allowed to react for 45 minutes. The reaction mixture is extracted 4 times with 3 ml of ethyl acetate and the ethyl acetate layer is washed with 5 ml of saturate saline solution. The washing is dried with sodium bicarbonate and concentrated under reduced pressure to obtain 107.1 mg of a crude acyl compound [B]. The compound is dissolved in 4.5 ml of 50% acetic acid and the solution is stirred at a temperature of 50° to 55° C. for 45 minutes. The solution is then cooled to room temperature and the deposited white precipitate is removed by filtration. The cake is washed with 2 ml of 50% acetic acid. The filtrate and the washing are combined and concentrated under reduced pressure. The residue is dissolved in a small amount of dimethylsulfoxide and charged on a column packed with 10 ml of HP-10. Elution is carried out with a mixture of water and methanol (5:1 to 2:1). Fractions showing an Rf value of 0.54 by silica gel thin layer chromatography (the same condition hereinbefore is used) are combined and concentrated under reduced pressure to obtain 12.9 mg (yield 23.8%) of white crystals of the desired compound having the following properties:

m.p. about 180° C. (decomposition).

$[\alpha]_D^{15°} -27°$ (DMSO, c=0.5).

IR (KBr)$\nu_{max}^{cm-1}$: 1770, 1672, 1633, 1540.

PMR(DMSO-d$_6$)δ: 9.26(1H, d, J=8.3), 7.18(2H, s), 6.75(1H, s), 6.31(1H, d, J=5.1), 5.51(1H, d-d, J=8.3, 5.0), 3.83(3H, s), 1.67(2H, m), 1.07(3H, d, J=7.3).

These values coincide well with those of the corresponding dl-compound. From the strong antimicrobial activity, absolute configuration of this compound is assumed to be (4S, 6R, 7S).

EXAMPLE 3

Preparation of (+)-cis-7-[2-(2-amino-4-thiazolyl)-2-syn-methoxyiminoacetamido]-1-azabicyclo[4,2,0] oct-2-en-8-on-2-carboxylic acid sodium salt by the following steps.

In this example, 200 mg (0.548 m mole) of (+)-cis-7-[2-(2-amino-4-thiazolyl)-2-syn-methoxyiminoacetamido]-1-azabicyclo[4,2,0]oct-2-en-8-on-2-carboxylic acid obtained as in Example 1 and 46 mg (0.548 m mole) of a powdered sodium bicarbonate are added into 1 ml of deionized water with stirring under ice cooling to obtain a clear solution. The solution is passed through a column packed with Diaion HP-10 and elution is carried out with water. Then, 8 ml of the first eluted fractions is discarded and the fractions eluted thereafter are combined and concentrated. The concentrate is lyophilized to obtain 195.8 mg (92.3%) of a white powder having the following properties.

$[\alpha]_D^{21°} = +46.4°$ (H$_2$O, c=0.5).

IR $\nu_{max}^{KBr}$(cm$^{-1}$): 3460, 1780(sh), 1770, 1760(sh), 1675, 1665, 1645, 1590, 1540.

NMR(D$_2$O)δ: 6.94(1H, s), 6.20(1H, t, J=4.2 Hz), 5.50(1H, d, J=4.9 Hz), 3.98(3H, s), 4.07–3.88 (1H, m), 2.41–1.46(4H, m).

EXAMPLE 4

Preparation of (−)-cis-7-[2-(2-amino-4-thiazolyl)-2-syn-(2-carboxyprop-2-oxyimino)acetamido]-1-azabicyclo[4,2,0]oct-2-en-8-on-2-carboxylic acid {or (6R,7S)-7-[2-(2-amino-4-thiazolyl)-2-syn-(2-carboxyprop-2-oxyimino)acetamido]-1-azabicyclo[4,2,0]oct-2-en-8-on-2-carboxylic acid}:

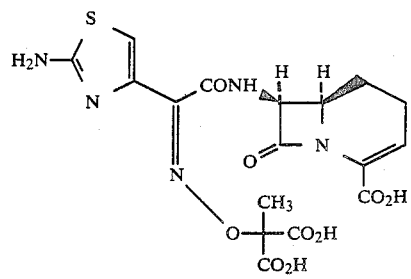

To the solution of phosphorus pentachloride (86 mg, 0.413 m mole) in 4 ml of anhydrous methylene dichloride is added 200 mg (0.384 m mole) of 2-(2-triphenylmethylaminothiazol-4-yl)-2-syn-(2-t-butyloxycarbonylprop-2-oximino)acetic acid at 0° C. The solution is stirred for 30 minutes, followed by addition of triethylamine [0.126 ml (0.903 m mole)].

The mixture is stirred for 5 minutes, evaporated in vacuo and dissolved in 20 ml of anhydrous tetrahydrofuran to make an acid chloride solution.

On the other hand, 50 mg (0.274 m mole) of (+)-cis-7-amino-1-azabicyclo[4,2,0]oct-2-en-8-on-2-carboxylic acid is dissolved in 6 ml of water and 3.5 ml of tetrahydrofuran and adjusted to pH 8 with triethylamine. To this solution is added the acid chloride solution prepared above under ice-cooling, maintaining the pH at 8–10 with triethylamine. After stirring for 3 hours under ice-cooling, another acid chloride solution (0.7eq.) prepared as before is added. The reaction mixture is stirred for one hour, evaporated in vacuo to remove tetrahydrofuran, and acidified to pH 2 with 2N HCl. Then, the mixture is saturated with sodium chloride and extracted with 30 ml of ethyl acetate three times. Extracts are washed with saturated aqueous sodium chloride solution, dried over sodium sulfate and evaporated in vacuo to afford 421 mg of yellow solid, which is then purified by chromatography (SiO$_2$ 10 g, solvent CHCl$_3$:CH$_3$OH=50:1) to give 256 mg of a protected acyl compound. This is treated with 5 ml of trifluoroacetic acid at room temperature for 20 minutes, followed by addition of 2 ml of water and 5 minutes later is concentrated to give yellow slurry which is purified through HP-10 column (50 ml).

| Elution:fraction | 1 | 200 ml (H$_2$O only) |
|---|---|---|
| | 2 | 150 ml (H$_2$O:MeOH 10:1) |
| | 3 | 100 ml (H$_2$O:MeOH 8:1) |
| | 4 | 200 ml (H$_2$O:MeOH 6:1) |
| | 5 | 200 ml (H$_2$O:MeOH 4:1) |
| | 6 | 90 ml (H$_2$O:MeOH 2:1) |
| | 7 | 600 ml (H$_2$O:MeOH 1:3) |

Fraction 7 is concentrated to dryness to afford 73.4 mg of crude product which is further purified by crystallization from methanol-water to give 30.9 mg (25.6%) of light yellow crystals. Properties of the product are as follows.

IR $\nu_{max}^{cm-1}$(KBr): 1770, 1760, 1680(sh), 1660, 1630.

NMR(DMSO-d$_6$)δ: 9.16(1H, d, J=8.3 Hz), 7.25(3H, s), 6.72(1H, s), 6.66(1H, br), 5.45(1H, dd, J=4.9, 8.3 Hz), 4.0–3.6(1H, m), 2.0–1.4(2H, m), 1.41(6H, s).

$[\alpha]_D^{25°} = -6.9°$ (c=1.0, CH$_3$OH).

EXAMPLE 5

Preparation of (+)-cis-7-[2-(2-amino-5-bromo-4-thiazolyl)-2-syn-methoxyiminoacetamido]-1-azabicyclo[4,2,0]oct-2-en-8-on-2-carboxylic acid:

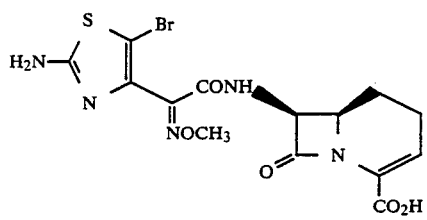

In this Example, 209 mg (0.40 m mole) of 2-(2-tritylamino-5-bromo-4-thiazolyl)-2-syn-methoxyiminoacetic acid is dissolved in 2 ml of anhydrous tetrahydrofuran and 56 μl (0.40 m mole) of triethylamine is added at a temperature of −20° C. After adding 83 mg (0.40 m mole) of a phosphorus pentachloride, the mixture is allowed to react with stirring at −20° C. for 40 minutes.

Separately, 60 mg (0.286 m mole) of (+)-cis-7-amino-1-azabicyclo[4,2,0]oct-2-en-8-on-2-carboxylic acid obtained as in Reference Example 2 is dissolved in a mixture of 6 ml of tetrahydrofuran and 6 ml of water, and 168 μl (1.20 m mole) of triethylamine is added. The acid chloride solution prepared above is added dropwise to the solution with stirring under ice cooling and further 30 μl of triethylamine is added. The mixture is allowed to react for two hours under ice cooling. Then, the mixture is adjusted to pH 2.0 with 1N hydrochloric acid and extracted twice with 10 ml of ethyl acetate. The ethyl acetate layers are washed with 20 ml of saturated saline solution, dried over sodium sulfate and concentrated under reduced pressure. The residue is dissolved in 10 ml of 50% aqueous acetic acid and stirred at a temperature of 50° C. for 30 minutes. After the concentration, the residue is dissolved in 10 ml of water and the solution is washed with 10 ml of ethyl acetate. The aqueous layer is charged on a column packed with 30 ml of Diaion HP-10 and elution is carried out with a mixture of water and methanol (10:1 to 4:1). Fractions showing and Rf value of 0.54 by silica gel thin layer chromatography (solvent: butanol:acetic acid:-water=4:1:1) are combined and concentrated under reduced pressure to give 56.3 mg of a white powder (yield 42.3%). Properties of the product are as follows:

IR νmax(KBr)(cm$^{-1}$): 3460, 1770, 1670, 1640, 1545.
NMR(CD$_3$OD)δ: 6.07(1H, m), 5.43(1H, d, J=5.1 Hz), 3.97(3H, s), 2.5–1.8(4H, m).
[α]$_D^{25°}$ = +48.0° (c=0.4, methanol).

REFERENCE EXAMPLE 1

Antimicrobial activities of the compounds obtained in Examples 1 and 2 are as follows. Heart Infusion Agar Dilution Method (ph 7.2) is used. The cephalosporin compound having the same acyl side chain (corresponding to the dl-compound) is used as a control.

A: The compound obtained in Example 1
A′: The dl-compound corresponding to the compound obtained in Example 1
B: The compound obtained in Example 2
B′: The dl-compound corresponding to the compound obtained in Example 2
C: Cephalosporin compound represented by the following formula.

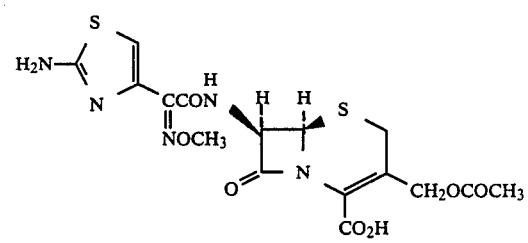

TABLE 2

| Microorganism | MIC (pg/m) | | | | |
|---|---|---|---|---|---|
| | A | A′ | B | B′ | C |
| Staphylococcus aureus 209-P | 3.12 | 12.5 | 1.56 | 6.25 | 0.78 |
| Staphylococcus aureus Smith | 6.25 | 25 | 6.25 | 12.5 | 1.56 |
| Staphylococcus epidermidis | 12.5 | 25 | 3.12 | 12.5 | 1.56 |
| Escherichia coli NIHJC-2 | 0.02 | 0.05 | 0.02 | 0.05 | 0.1 |
| Escherichia coli GN2411-5 | 0.01 | 0.05 | ≦0.01 | 0.02 | 0.05 |
| Escherichia coli Juhl | 0.02 | 0.1 | 0.02 | 0.05 | 0.05 |
| Klebsiella pneumoniae 8045 | ≦0.006 | ≦0.006 | ≦0.01 | 0.01 | ≦0.01 |
| Klebsiella pneumoniae Y-60 | 0.02 | 0.05 | 0.02 | 0.05 | 0.05 |
| Serratia marcescens T-26 | 0.2 | 0.78 | 0.4 | 0.78 | 0.78 |
| Serratia marcescens T-55 | 0.02 | 0.1 | 0.05 | 0.2 | 0.1 |
| Proteus mirabilis 1287 | 0.01 | 0.02 | ≦0.01 | 0.01 | 0.02 |
| Proteus vulgaris 6897 | ≦0.006 | 0.01 | ≦0.01 | 0.01 | ≦0.01 |
| Proteus morganii KY 4298 | 0.05 | 0.1 | 0.02 | 0.1 | 0.05 |
| Proteus rettgeri KY 4289 | ≦0.006 | ≦0.006 | ≦0.01 | 0.01 | ≦0.01 |
| Pseudomonas aeruginosa #1 | 6.25 | 25 | 25 | 50 | 6.25 |
| Pseudomonas aeruginosa 145 | 50 | 50 | 100 | >100 | 50 |
| Pseudomonas putida 264 | 0.1 | 0.4 | 0.05 | 0.2 | 0.1 |

REFERENCE EXAMPLE 2

Preparation of (+)-cis-7-amino-1-azabicyclo[4,2,-0]oct-2-en-8-on-2-carboxylic acid {or (6R,7S)-7-amino-1-azabicyclo[4,2,0]oct-2-en-8-on-2-carboxylic acid}:

In this example the following steps are performed.

Cultivation of a microorganism having an ability of optical selective deacylation As the seed strain, Kluyvera citrophila ATCC 21285 [Biological properties are described in J. General Applied Microbiology 3, 28–31 (1957)] is used.

As the seed medium, an aqueous solution containing 1% polypeptone, 1% yeast extract, 0.5% meat extract, 0.5% sodium glutamate and 0.25% sodium chloride and adjusted at a pH of 7.0 with 5N-NaOH is used. One loopful of the seed strain is inoculated into 10 ml of the seed medium in 50 ml of a large test tube and culturing is carried out at a temperature of 30° C. for 24 hours. All of the seed broth is then inoculated into 300 ml of the culture medium in 2 l of an Erlenmeyer flask and culturing is carried out at a temperature of 30° C. with shaking. The composition of the culture medium is the same as that of the seed medium.

Preparation of disrupted cell suspension

After culturing for 24 hours, the culture broth is subjected to centrifugation to obtain cell bodies. The cells are washed twice with 50 ml of 0.9% saline solution and suspended in a concentration of 40 mg/ml by dry weight in 1/30M phosphate buffer solution. Then, 10 ml of the cell suspension is put into 50 ml of a large test tube and subjected to ultrasonic disintegration at 200 W for 2 minutes to obtain a disrupted cell suspension. In the treatment, an ultrasonic disintegrator Model UR200P (product of Tomy Seiko Co., Ltd.) is used.

Preparation of a substrate solution

In this step, 200 mg of (±)cis-7-phenylacetamido-1-azabicyclo[4,2,0]oct-2-en-8-on-2-carboxylic acid obtained as in GO No. 2911787 is added into 9 ml of 1/30M phosphate buffer (pH 6.5). Since the compound is not dissolved, a small portion of 2N-NaOH is added and the mixture is again adjusted to a pH of 6.5 to dissolve the compound. Finally, deionized water is added to make up 10 ml of a solution.

Enzyme reaction

In this step, 10 ml of the disrupted cell suspension mentioned above is added to 10 ml of the substrate solution and enzyme reaction is carried out at a temperature of 30° C. for 80 minutes. The time course of the reaction is illustrated in the following Table 3.

TABLE 3

| Reaction period (minutes) | The amount of Compound (III-1) produced (mg/ml) | Yield (Mol ratio, %) |
| --- | --- | --- |
| 10 | 2.0 | 33 |
| 20 | 2.6 | 43 |
| 40 | 2.9 | 48 |
| 60 | 3.0 | 50 |
| 80 | 3.0 | 50 |

As apparent from the Table 3, the reaction and yield are stationary since the conversion ratio of the mixture of the optically active isomers reaches 50% (mol ratio).

Isolation and Purification of the desired compound

After the completion of the reaction, the microbial cells are removed by centrifugation from the reaction solution. The supernatant is adjusted to a pH of 3.0 with 2N-hydrochloric acid and charged on a column (2.6 cm diameter, 51 cm height) packed with 270 ml of Diaion HP-10. Elution is carried out with deionized water and the eluate is collected in 5 ml fractions. The desired compound is eluted out in the fractions from 280 ml to 315 ml. These fractions are concentrated under reduced pressure, lyophilized and dissolved in a small amount of a mixture of water and methanol (50:50 by volume, the same shall apply hereinafter). The solution is charged on a column (1.6 cm diameter, 64.5 cm height) packed with 130 ml of Sephadex LH 20 (Farmaci Fine Chemicals Inc.). Elution is carried out with a mixture of water and methanol (50:50). The elute is collected in 5 ml fractions, and the fractions from 65 ml to 85 ml are combined and concentrated under reduced pressure to remove methanol. Then, the residue is lyophilized to obtain 48 mg of a white powder having the following properties.

IR(KBr) $v_{max}^{cm^{-1}}$: 1800, 1790, 1775, 1640, 1620.

NMR(100M D$_2$O-DSS)δ: 6.46(1H, dd, J=3.5, 4.7 Hz), 4.88(1H, d, J=5.2 Hz), 4.06(1H, m), 2.5–1.5(4H, m).

It is determined that the compound has one mole of hydrochloric acid and water. The properties of the compound coincide well with those of the corresponding dl-compound. The value of optical rotation is $[\alpha]_D^{15°} = +48°$ [c=0.5, in 1M phosphate buffer solution (pH 7.0)] which coincides well with the value in Reference Example 3 below, $[\alpha]_D^{15°} = +48.5°$ [c=0.5, in 1M phosphate buffer solution (pH 7.0)].

The compound shows a ninhydrin positive single spot at an Rf value of 0.22 on silica gel thin layer chromatography [thin layer plate Merck Art 5721 (product of E. Merck & Co.), solvent for development, isopropanol:acetic acid:water=4:1:1]. The Rf value coincides with that of the optically inactive dl-compound.

REFERENCE EXAMPLE 3

Preparation of (+)-cis-7-amino-1-azabicyclo[4,2,0]oct-2-en-8-on-2-carboxylic acid (Alternative method)

Preparation of disrupted cell suspension

The same procedure as in Reference Example 2 is repeated.

Preparation of a substrate solution

In this step, 100 mg of (+)-cis-7-[(R)-2-phenyl-2-aminoacetamido]-1-azabicyclo[4,2,0]oct-2-en-8-on-2-carboxylic acid obtained as in GO No. 2911787 is disolved in 5 ml of 1/30M phosphate buffer solution (pH 6.5).

Enzyme reaction

In this step, 5 ml of the disrupted cell suspension mentioned above is added in 5 ml of the substrate solution and enzyme reaction is carried out at 30° C. for 24 hours.

Isolation and Purification

In this step, 46mg of a white powder is obtained by a similar method as in Reference Example 2. Properties of the compound coincide well with those of the compound obtained in Reference Example 2.

$[\alpha]_D^{15°} = +48.5°$ [c=0.5, in 1M phosphate buffer solution (pH 7.0)].

REFERENCE EXAMPLE 4

Preparation of (−)-cis-7β-amino-4α-methyl-1-azabicyclo[4,2,0]oct-2-en-8-on-2-carboxylic acid:

Preparation of disrupted cell suspension

A similar procedure as in Reference Example 2 is repeated.

Preparation of a substrate solution

A similar procedure as in Reference Example 2 is repeated except that (±)-cis-7β-phenylacetamido-4α-methyl-1-azabicyclo[4,2,0]oct-2-en-8-on-2-carboxylic acid obtained as in GO No. 2911787 is used.

Enzyme reaction

A similar procedure as in Reference Example 2 is repeated except that the disrupted cell suspension and the substrate solution obtained in the above are used. The reaction ratio become stationary in one hour. The reaction is continued for 120 minutes. The yield is 50% (mol ratio) of the mixture of optically active compounds.

Isolation and Purification

An almost similar procedure as in Reference Example 2 is repeated. After the completion of reaction, the microbial cells are removed by centrifugation from the reaction solution. The supernatant is then charged on a column (2.5 cm diameter, 46 cm height) packed with 220 ml of Diaion HP-10. Elution is carried out with deionized water and the elute is collected in 5 ml fractions. The desired compound is eluted in the fractions from 200 ml to 270 ml. These fractions are concentrated under reduced pressure, lyophilized, and dissolved in a small amount of water and methanol (50:50). The solution is then charged on a column (1.6 cm diameter, 64.5 cm height) packed with 130 ml of Sephadex LH-20 and elution is carried out with a mixture of water and methanol (50:50). The elute is collected in 5 ml fractions. The fractions from 65 ml to 80 ml are combined and concentrated to remove methanol. Then, the residue is lyophilized to obtain 30.5 mg of a white powder. Properties of the compound are as follows.

IR(KBr) $\nu_{max}cm^{-1}$: 1800, 1770(sh), 1760(sh), 1740, 1680, 1630.

NMR(100M D$_2$O-DSS)$\delta$: 6.16(1H, d, J=5.1 Hz), 4.52(1H, d, J=4.9 Hz), 3.86(1H, m), 2.64(1H, m), 1.9–1.4(2H, m), 1.10(3H, d, J=7.3 Hz).

It is determined that the compound is a potassium salt having 2 moles of water. The properties above coincide well with those of the corresponding dl-compound. The compound shows a ninhydrin positive single spot at Rf=0.33 on a silica gel thin layer chromatography (the same silica gel as in Example 1 is used). The Rf value coincides with that of the optically inactive dl-compound.

Optical rotation $[\alpha]_D^{15°} = -30°$ (c=0.5, in 1M phosphate buffer solution). The value coincides well with that in Reference Example 5, $[\alpha]_D^{15°} = -30.8°$ [c=0.5, in 1M phosphate buffer solution (pH 7.0)].

REFERENCE EXAMPLE 5

Preparation of (−)-cis-7β-amino-4α-methyl-1-azabicyclo[4,2,0]oct-2-en-8-on-2-carboxylic acid (Alternative method).

Preparation of disrupted cell suspension

A similar procedure as in Reference Example 4 is repeated.

Preparation of a substrate solution

In this step, 100 mg of (+)-cis-7β-[(R)-2-phenyl-2-aminoacetamido]-4α-methyl-1-azabicyclo[4,2,0]oct-2-en-8-on-2-carboxylic acid obtained as in GO No. 2911787 is dissolved in 5 ml of 1/30M phosphate buffer solution.

Enzyme reaction

In this step, 5 ml of the disrupted cell suspension described above is added to 5 ml of the substrate solution and enzyme reaction is carried out at a temperature of 30° C. for 24 hours.

Isolation and Purification

A similar procedure as in Reference Example 4 is repeated to obtain 55 mg of a white powder. Properties of the compound coincide well with those in Reference Example 4.

Optical rotation $[\alpha]_D^{15°} = -30.8°$ [c=0.5, in 1M phosphate buffer solution (pH 7.0)].

What is claimed is:

1. A compound of the formula:

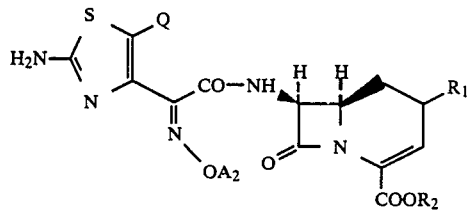

wherein R$_1$ represents a hydrogen or a lower alkyl group having 1 to 5 carbon atoms;

R$_2$ represents a hydrogen or a protective group of carboxylic acid selected from straight or branched lower alkyl groups having 1 to 5 carbon atoms, straight or branched lower alkoxymethyl groups having 1 to 5 carbon atoms, straight or branched halogenated alkyl groups having 1 to 5 carbon atoms, lower alkylsulfonylethyl groups, arylmethyl groups having 7 to 12 carbon atoms, a benzyl, diphenylmethyl or triphenylmethyl group and a group represented by the formula:

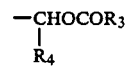

wherein R$_3$ is a straight or branched lower alkyl group having 1 to 6 carbon atoms, a straight or branched lower alkoxy group having 1 to 6 carbon atoms or a phenyl group; and R$_4$ is a hydrogen or a straight or branched lower alkyl group having 1 to 6 carbon atoms, Q represents a hydrogen or a halo group selected from bromo, chloro, fluoro and iodo;

A$_2$ represents a hydrogen, a lower alkyl group having 1 to 6 carbon atoms, a lower alkenyl group having 2 to 6 carbon atoms, a lower alkinyl group having 2 to 6 carbon atoms, which groups are unsubstituted or mono-substituted with a suitable substituent selected from the group consisting of carboxyl, cyano, halo, carbamoyl, and lower alkyloxycarbonyl having 1 to 5 carbon atoms; and pharmaceutically acceptable salts thereof.

2. The compound according to claim 1 wherein A$_2$ is a lower alkyl group having 1 to 6 carbon atoms or a substituted lower alkyl group having carboxyl group as substituent and OA$_2$ group has syn configuration.

3. The compound according to claim 2, wherein A$_2$ is a methyl group.

4. The compound according to claim 3, wherein R$_1$ is a hydrogen.

5. The compound according to claim 4, wherein R$_2$ and Q are a hydrogen, that is, (+)-cis-7-[2-(2-amino-4-thiazolyl)-2-syn-methoxyiminoacetamido]-1-azabicyclo[4,3,0]oct-2-en-8-on-2-carboxylic acid or its sodium salt.

6. The compound according to claim 4, wherein $R_2$ is a hydrogen and Q is a bromo group, that is, (+)-cis-7-[2-(2-amino-5-bromo-4-thiazolyl)-2-syn-methoxyiminoacetamido]-1-azabicyclo[4,2,0]oct-2-en-8-on-2-carboxylic acid.

7. The compound according to claim 2, wherein Q is a hydrogen and $A_2$ is a 2-carboxy-2-prop-2-yl group.

8. The compound according to claim 7, wherein $R_1$ is a hydrogen.

9. The compound according to claim 8, wherein $R_2$ is a hydrogen, that is, (−)-cis-7-[2-(2-amino-4-thiazolyl)-2-syn-(2-carboxyprop-2-oxyimino)acetamido]-1-azabicyclo[4,2,0]oct-2-en-8-on-2-carboxylic acid.

10. The compound according to claim 3, wherein $R_1$ is a methyl group.

11. The compound according to claim 10, wherein $R_2$ is a hydrogen.

12. The compound according to claim 11, wherein the methyl group at the 4-position has the same configuration as the hydrogens at the 6- and 7-positions, that is (−)-cis-7β-[2-(2-amino-4-thiazolyl)-2-syn-methoxyiminoacetamido]-4α-methyl-1-azabicyclo[4,2,0]oct-2-en-8-on-2-carboxylic acid.

13. The sodium salt of the compound in claim 5.

* * * * *

UNITED STATES PATENT AND TRADEMARK OFFICE
CERTIFICATE OF CORRECTION

PATENT NO.   : 4,755,596
DATED        : July 5, 1988
INVENTOR(S)  : Tadashi Hirata et al.

It is certified that error appears in the above-identified patent and that said Letters Patent is hereby corrected as shown below:

Column 9, line 48, "crude compound [A]." should read

-- crude acyl compound [A]. --.

Signed and Sealed this

Thirty-first Day of January, 1989

Attest:

DONALD J. QUIGG

Attesting Officer

Commissioner of Patents and Trademarks